United States Patent
Abdelsalam et al.

(10) Patent No.: US 9,730,762 B2
(45) Date of Patent: Aug. 15, 2017

(54) AUTOMATIC NEEDLE INSERTION LOCATION IDENTIFICATION

(71) Applicant: NeoCoil, LLC, Pewaukee, WI (US)

(72) Inventors: Emad Abdelsalam, Milwaukee, WI (US); Paul Ropella, New Berlin, WI (US); Brian Brown, Wauwatosa, WI (US); Steven Wolff, New York, NY (US)

(73) Assignee: Neocoil, LLC, Pewaukee, WI (US)

( * ) Notice: Subject to any disclaimer, the term of this patent is extended or adjusted under 35 U.S.C. 154(b) by 540 days.

(21) Appl. No.: 13/833,593

(22) Filed: Mar. 15, 2013

(65) Prior Publication Data

US 2014/0275971 A1  Sep. 18, 2014

(51) Int. Cl.

| | | |
|---|---|---|
| *A61B 19/00* | (2006.01) | |
| *A61B 90/17* | (2016.01) | |
| *G01R 33/28* | (2006.01) | |
| *A61B 34/20* | (2016.01) | |
| *A61M 5/42* | (2006.01) | |
| *A61N 5/10* | (2006.01) | |
| *G01R 33/36* | (2006.01) | |
| *A61B 17/34* | (2006.01) | |

(Continued)

(52) U.S. Cl.
CPC .......... *A61B 90/17* (2016.02); *A61B 17/3403* (2013.01); *A61B 34/20* (2016.02); *G01R 33/28* (2013.01); *A61B 10/0275* (2013.01); *A61B 2017/00221* (2013.01); *A61B 2017/3411* (2013.01); *A61B 2090/0811* (2016.02); *A61M 5/427* (2013.01); *A61N 2005/1012* (2013.01); *G01R 33/3692* (2013.01)

(58) Field of Classification Search
CPC .......... A61B 2017/3411; A61M 5/427; A61N 2005/1012
See application file for complete search history.

(56) References Cited

U.S. PATENT DOCUMENTS

| | | |
|---|---|---|
| 5,855,554 A | 1/1999 | Schneider et al. |
| 5,961,457 A | 10/1999 | Raylman et al. |

(Continued)

OTHER PUBLICATIONS

Glossop et al. "Laser projection augmented reality system for computer assisted surgery." Medical Image Computing and Computer-Assisted Intervention-MICCAI 2003. Springer Berlin Heidelberg, 2003. 239-246.*

*Primary Examiner* — David J McCrosky
(74) *Attorney, Agent, or Firm* — Boyle Fredrickson, SC (57) ABSTRACT

A system for automatically identifying a needle insertion location from a medical diagnostic image, such as an MRI image, and providing a visual indication of the needle insertion location is disclosed. A grid plate is located proximate to an anatomical region and is preferably incorporated in an MRI support structure utilized to immobilize the anatomical region. An MRI scanner obtains an MRI image of the anatomical region, and an MRI technician places a marker on the MRI image, identifying the needle insertion location. The MRI image and the marker are transferred from the MRI scanner to another device, such as a tablet computer, which is configured to convert the MRI image and the marker to coordinates and an insertion depth. A visual indicator is located proximate to or integrated with the grid plate that provides the needle insertion coordinates and insertion depth to the MRI technician.

21 Claims, 6 Drawing Sheets

(51) Int. Cl.
*A61B 17/00* (2006.01)
*A61B 10/02* (2006.01)
*A61B 90/00* (2016.01)

(56) References Cited

U.S. PATENT DOCUMENTS

| | | | |
|---|---|---|---|
| 6,423,076 B1 * | 7/2002 | Cardwell et al. | 606/130 |
| 6,714,628 B2 | 3/2004 | Broyles et al. | |
| 6,869,390 B2 * | 3/2005 | Elliott et al. | 600/1 |
| 6,889,073 B2 | 5/2005 | Lampman et al. | |
| 6,904,305 B2 | 6/2005 | Tsekos | |
| 7,379,769 B2 | 5/2008 | Piron et al. | |
| 7,438,692 B2 | 10/2008 | Tsonton et al. | |
| 7,831,290 B2 | 11/2010 | Hughes et al. | |
| 8,175,677 B2 | 5/2012 | Sayler et al. | |
| 8,206,314 B2 | 6/2012 | Mollere | |
| 8,235,909 B2 | 8/2012 | Barthe et al. | |
| 8,303,505 B2 | 11/2012 | Webler et al. | |
| 8,308,740 B2 | 11/2012 | Tolley et al. | |
| 8,315,689 B2 | 11/2012 | Jenkins et al. | |
| 8,328,732 B2 | 12/2012 | Parihar et al. | |
| 8,340,743 B2 | 12/2012 | Jenkins et al. | |
| 8,369,930 B2 | 2/2013 | Jenkins et al. | |
| 8,374,677 B2 | 2/2013 | Piferi et al. | |
| 8,905,610 B2 * | 12/2014 | Coleman et al. | 362/554 |
| 2007/0043291 A1 * | 2/2007 | Fidel et al. | 600/439 |
| 2009/0234302 A1 * | 9/2009 | Hoendervoogt et al. | 604/288.01 |
| 2012/0065454 A1 * | 3/2012 | Kader et al. | 600/8 |
| 2012/0203095 A1 * | 8/2012 | Krieger et al. | 600/411 |
| 2014/0213886 A1 | 7/2014 | Menon et al. | |

\* cited by examiner

AUTOMATIC NEEDLE INSERTION LOCATION IDENTIFICATION

BACKGROUND OF THE INVENTION

The subject matter disclosed herein relates to a system and method for identifying a needle insertion location, and more specifically, for automatically providing a visual indication of the needle insertion location during a procedure performed in coordination with a medical diagnostic image, such as a magnetic resonance imaging (MRI) image.

As is known to those skilled in the art, an MRI system alternately generates a strong magnetic field and then detects the faint nuclear magnetic resonance (NMR) signals given off by nuclei in the presence of the magnetic field. The NMR signals vary as a function of the type of organ, bone, tissue, etc. . . . present within the magnetic field. The NMR signals are received by antennas, also known as coils, and transmitted to the MRI scanner for reconstruction into an MRI image. Specifically, an anatomical region of a patient is located within the magnetic field and proximate to the antennas. The MRI scanner reconstructs the NMR signals into an MRI image corresponding to the anatomical region of the patient being imaged.

Figure 1:
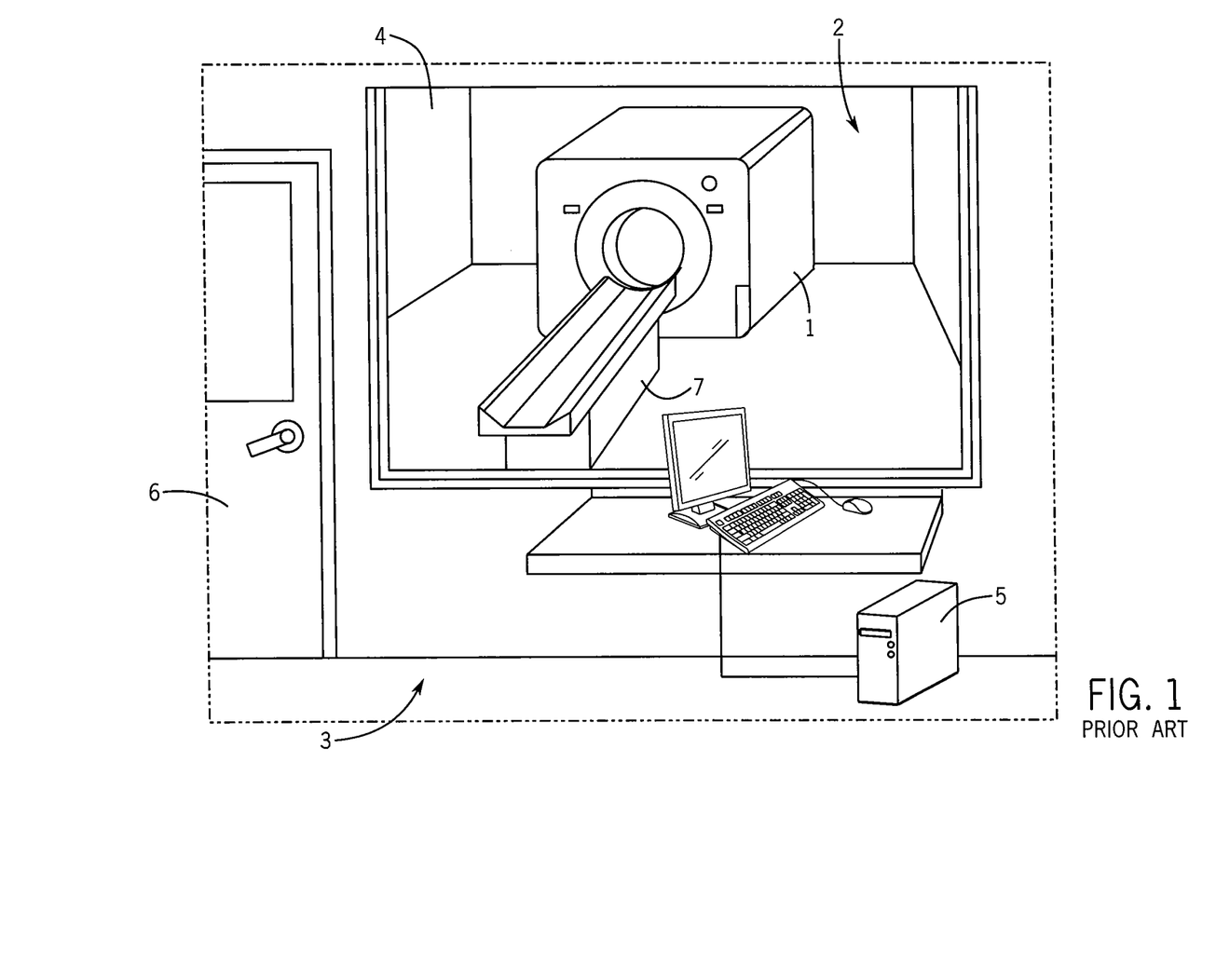
FIG. 1 is an exemplary MRI scan room and control room.

For reference, an exemplary MRI scan room 2 and control room 3 are illustrated in FIG. 1. The MRI scan room 2 is connected to the MRI control room 3 via a door 6 and typically provides a window 4 from which the MRI technician may observe the MRI procedure. A patient is positioned on an MRI table 7, a portion of which may be slid into a bore of an MRI scanner 1. The MRI scanner 1 is controlled via a control unit 5, such as a computer executing control software, located in the control room 3.

In some medical procedures an MRI scanner may be used to facilitate positioning the patient and/or a medical instrument during the procedure. For example, a biopsy procedure may be administered with the aid of an MRI scanner. The patient is positioned on a table and the anatomical region from which a biopsy sample is to be obtained may be immobilized. The MRI scanner obtains an MRI image of the anatomical region and an MRI radiologist identifies the location within the image from which the biopsy sample is to be taken. This location is recorded and the coordinates recorded on a worksheet. The MRI radiologist, or other medical personnel, may use the coordinates to locate the insertion point for the biopsy needle on the immobilized anatomical region. Optionally, the region may be reimaged with the biopsy needle inserted to verify that the needle is at the correct location and/or to make adjustments to the position of the biopsy needle prior to obtaining the biopsy sample from the patient.

However, the process of identifying the biopsy location and positioning the biopsy needle is not without drawbacks. The process of transferring the biopsy location from an MRI image to a worksheet and using the worksheet to identify the needle insertion location on the patient has a risk of error. Further, the process is time consuming and may require repetition to precisely locate the needle within the desired biopsy location. Thus, it would be desirable to provide a system to automatically identify a biopsy location and to automatically present a visual indication of the identified location to medical personnel.

BRIEF DESCRIPTION OF THE INVENTION

The subject matter disclosed herein describes a system for automatically identifying a location from a medical diagnostic image, such as an MRI image, and providing a visual indication of the location to the MRI technician or other medical personnel. A patient is positioned on an MRI table and an anatomical region of which an MRI image is desired is immobilized by, for example, a support structure. A grid plate is located proximate to the anatomical region and is preferably incorporated in the support structure utilized to immobilize the anatomical region. An MRI scanner obtains an MRI image of the anatomical region on which a medical procedure is to be performed. The MRI technician electronically places a marker on the MRI image, identifying the location of the procedure. The MRI image and the marker are transferred from the MRI scanner to another device, such as a tablet computer. Optionally, the MRI image is first transferred to the other device and the MRI technician places the marker on the image via a user interface on the other device. The tablet computer is configured to execute a program to convert the MRI image and the marker to a set of coordinates and an insertion depth which correspond to the identified location. A visual indicator is located proximate to or integrated with the grid plate that identifies the location on the grid plate at which the procedure is to be performed. A depth indication identifies, for example, the depth at which a biopsy needle is to be inserted at the identified location. The entire process is automated, such that upon obtaining an MRI image, the MRI technician or other medical personnel performing is presented a visual indication at the anatomical region identifying the location at which the procedure is to be performed.

According to one embodiment of the invention, a needle insertion location identification system is disclosed for use with a support structure. The support structure is configured to position a patient during a medical procedure guided by diagnostic imaging, such as a magnetic resonance imaging (MRI) guided procedure. The needle insertion location identification system includes a grid plate having a plurality of openings arranged in an array, and the grid plate is configured to be inserted into a portion of the support structure. A grid block is configured to be inserted into one of the openings in the grid plate. The grid block includes a plurality of apertures, where each aperture is configured to receive a needle. An interface unit is configured to communicate with a remote processor to receive needle insertion information, which identifies one of the openings and one of the apertures. A grid indication unit is configured to provide a visual indication of the opening and of the aperture identified by the needle insertion information. The needle insertion information may also include an insertion depth or a needle orientation, and the grid indication unit is further configured to provide a visual indication of the insertion depth or needle orientation, respectively.

According to another aspect of the invention, the needle insertion location identification system may also include a plurality of row indicia and a plurality of column indicia. Each of the row indicia corresponds to a row in the array, and each of the column indicia corresponds to a column in the array. The needle insertion information includes one of the row indicia and one of the column indicia, and the grid indication unit is configured to display each of the row indicia and the column indicia included in the needle insertion information.

According to still another aspect of the invention, the needle insertion location identification system may include a plurality of light guides and a plurality of light sources. At least one light guide extends along each row and each column of the array. Each light source corresponds to one of the light guides and is configured to emit light along the light guide. The grid indication unit is configured to control each of the light sources to emit light along the light guide extending along the row and the light guide extending along the column of the opening identified in the needle insertion information.

According to yet another aspect of the invention, the needle insertion location identification system may include a plurality of light sources wherein at least one of the light sources corresponds to each of the openings in the grid plate. Each of the light sources may be a light emitting diode (LED), and one of the LEDs is placed at each intersection between a row and a column in the array of openings. The visual indication of the opening is provided by energizing each of the LEDs placed at the intersections around the opening. The grid indication unit includes a plurality of LEDs arranged to correspond to an arrangement of the apertures in the grid block, and one of the LEDs is energized to provide the visual indication of the aperture identified by the needle insertion information.

According to still another aspect of the invention, the interface unit is configured to communicate wirelessly with the remote processor. A portable processing device may include the remote processor and may be configured to wirelessly receive at least one MRI image and at least one marker corresponding to a target area identified in one of the MRI images from a control unit of an MRI scanner. The portable processing device determines the insertion information as a function of the at least one MRI image and the at least one marker and transmits the insertion information to the grid indication unit. The portable processing device may be a laptop, notebook, or tablet computer or other such portable device.

According to another embodiment of the invention, a block identification system is disclosed for use with a support structure configured to position a patient during a medical procedure guided by diagnostic imaging, such as a magnetic resonance imaging (MRI) guided procedure. The block identification system includes a grid plate, including an outer periphery defined by a plurality of outer walls and a plurality of intersecting grid walls. Each grid wall extends between a first outer wall and a second outer wall, and the plurality of intersecting grid walls defines a plurality of openings therebetween. At least one grid block is configured to be inserted into one of the openings in the grid plate. The grid block includes a plurality of apertures, and a grid indication unit is configured to provide a visual indication of one of the openings and one of the apertures as a function of insertion information received from a remote processor. Optionally, multiple, or all, of the openings may include a grid block, and each grid block may be integrally formed with the grid plate.

According to another aspect of the invention, the plurality of openings defines a two-dimensional array. The block identification includes a first set of indicia identifying openings along a first dimension of the array and a second set of indicia identifying openings along a second dimension of the array. The grid indication unit displays one of the first set of indicia and one of the second set of indicia corresponding to the opening identified by the insertion information.

These and other objects, advantages, and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWING(S)

Various exemplary embodiments of the subject matter disclosed herein are illustrated in the accompanying drawings in which like reference numerals represent like parts throughout, and in which.

In describing the preferred embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

The various features and advantageous details of the subject matter disclosed herein are explained more fully with reference to the non-limiting embodiments described in detail in the following description.

Figure 2:
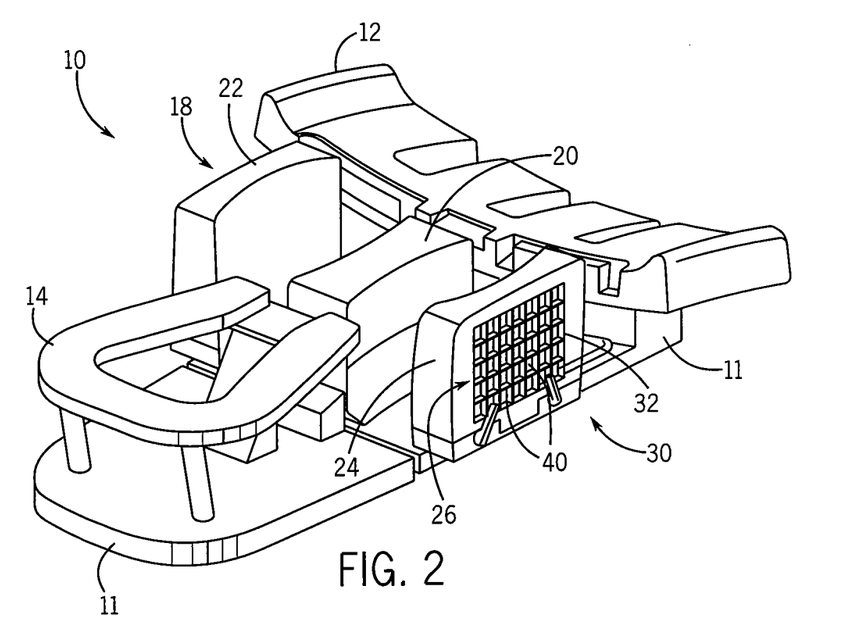
FIG. 2 is an isometric view of an exemplary support structure incorporating one embodiment of the invention.

Referring initially to FIG. 2, an exemplary support structure 10 for use in breast imaging is illustrated. The support structure 10 provides support for a patient while positioning the patient's breasts to obtain an MRI image. The support structure 10 includes an abdominal support member 12 and a head support member 14. Each of the abdominal support member 12 and head support member 14 are mounted on a base 11. The base 11 may be a single structure extending between the abdominal support member 12 and the head support member 14 or, as illustrated, the base 11 may include multiple segments, each support member mounted on one of the segments. In addition, imaging plates are mounted to the base 11. As illustrated, a central, stationary plate 20 and removable compression plates may be provided. Each compression plate may be used to secure a patient's between the respective compression plate 22 and the stationary plate 20. A first compression plate 22 is illustrated having a solid surface. A second compression plate 24 is illustrated having an opening 26 extending therethrough. The stationary plate 20 may include an antenna array, or multiple antenna arrays, one used for imaging each breast. It is contemplated that the compression plates are removable and configurable according to the application requirements. For example, an antenna array, which is configured to detect NMR signals and transmit the NMR signals back to the MRI control unit, may be enclosed within the first compression plate 22. A single antenna loop may be provided within the periphery of the second compression plate 24, the single antenna loop also being configured to detect NMR signals and transmit the NMR signals back to the MRI control unit. The opening 26 in the second compression plate 24 is configured to receive a grid plate 32, which is one element of a needle insertion location identification system as discussed in more detail below. Additional elements of the needle insertion location identification system may either be inserted or incorporated into the second compression plate 24.

Figure 3:
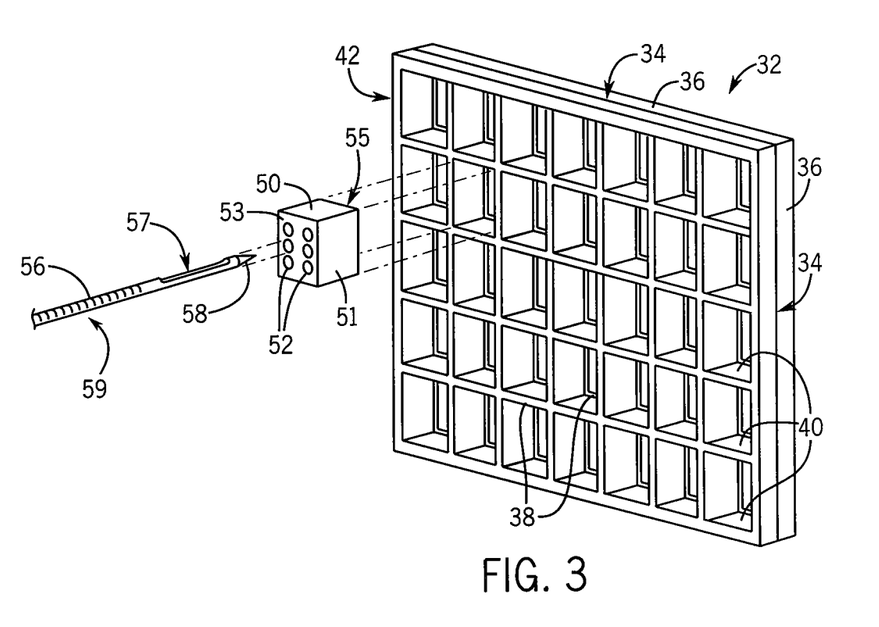
FIG. 3 is a partial exploded isometric view of the support structure of FIG. 2, illustrating one embodiment of a grid plate and a grid block.
Figure 4:
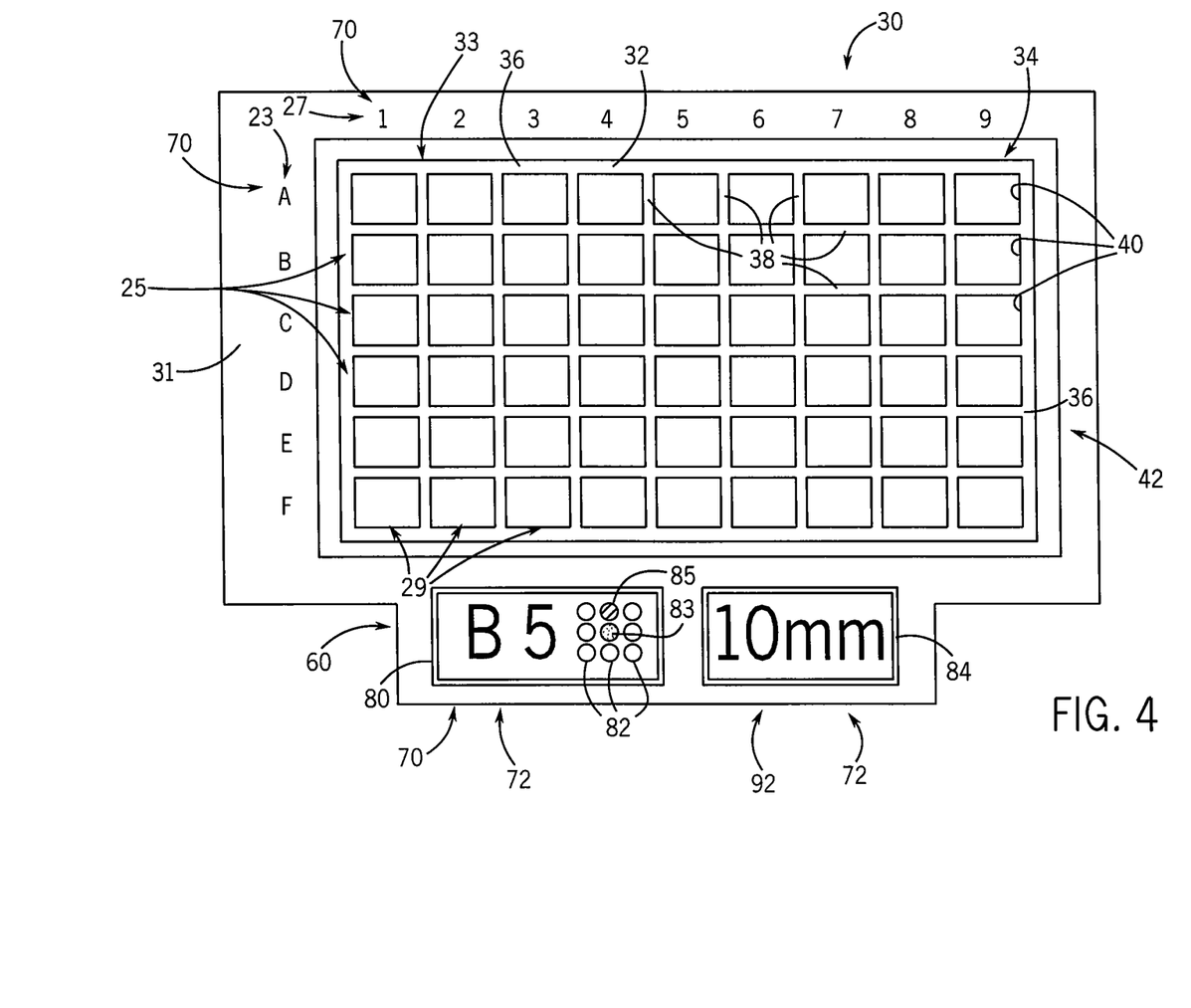
FIG. 4 is a front elevation view of a needle insertion system according to one embodiment of the invention.

Referring next to FIGS. 3 and 4, one embodiment of a needle insertion location system 30 is illustrated. The needle insertion location system 30 includes a grid plate 32 which defines an array 42 of openings 40 into which a grid block 50 may be inserted. The grid plate 32 includes an outer periphery 34 defined by a plurality of outer walls 36. According to the illustrated embodiment, the outer walls 36 define a rectangular outer periphery 34. However, it is contemplated that various other shapes may be formed without deviating from the scope of the invention. Intersecting grid walls 38, extending between opposite outer walls 36, define the openings 40 in the grid plate 32. The number and orientation of the grid walls 38 are arranged to define substantially uniform openings 40, such that the grid block 50 may be inserted into any of the openings 40. According to one embodiment of the invention, the grid plate 32 is a disposable element, replaced after each procedure. Optionally, the grid plate 32 may be configured to be sterilized and re-used for multiple procedures.

A grid block 50 is configured to be inserted into one of the openings 40 in the grid plate 32. The outer periphery 51 of the grid block 50 is complementary to the periphery of each opening 40 such that it is slidably received within the opening 40. Each grid block 50 includes multiple apertures 52 extending from a front surface 53 to a rear surface 55. According to one embodiment of the invention, the apertures 52 are cylindrical and configured to slidably receive a needle 56, such as a biopsy needle, for insertion into a patient. Optionally, the apertures 52 may be oval or any other shape, corresponding to the periphery of the needle and/or instrument to be inserted through the grid block 50. The grid block 50 is typically provided by the needle manufacturer to accept varying configurations and/or sizes of needles 56. As illustrated, the needle 56 may be cylindrical and include a pointed end 58 to facilitate insertion of the needle 56 into the anatomical region. An opening 57 along one side of the needle 56 is used to collect the tissue sample for biopsy. Gradations 59 along the length of the needle 56 are used to indicate to the MRI technician, nurse, or other medical personnel performing the biopsy the depth at which the needle is inserted into the patient. It is further contemplated that multiple grid blocks 50 may be provided to accommodate various sizes and/or shapes of the needle and/or instrument to be inserted. In addition, multiple grid blocks 50 having identical or varying size and/or shaped apertures 52 may be provided to allow multiple needles and/or instruments to be utilized during a single procedure.

Figure 8:
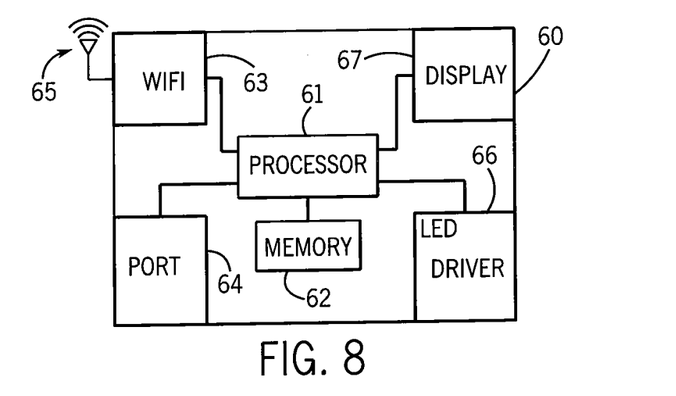
FIG. 8 is a block diagram representation of the interface unit of the needle insertion system of FIG. 7.

The needle insertion location identification system 30 further includes an interface unit 60 configured to communicate with a remote device. Referring also to FIG. 8, the interface unit 60 includes a processor 61 configured to execute a series of instructions stored in a memory device 62. It is contemplated that the processor 61 may be a single device or multiple devices executing in coordination with each other. The processor 61 may be of various configurations, including, but not limited to, a microprocessor or incorporated, for example, onto an application specific integrated circuit (ASIC) or a field-programmable gate array (FPGA). Similarly, the memory device 62 may be a single device or multiple devices and may be dynamic, persistent, or a combination thereof. The processor 61 is connected to a wireless module 63 configured to transmit and/or receive data using a Wi-Fi technology established, for example, by the IEEE 802.11 family of standards. Optionally, the wireless module 63 may be configured to transmit and/or receive data using any other suitable protocol established, for example, by the Bluetooth® standard. The wireless module transmits and/or receives communications via at least one antenna 65 connected to and typically integrated with the wireless communication module 63. Optionally, the antenna 65 may be a separate device either internal to or external from the interface unit 60. An additional port interface 64 may be provide to provide a wired connection to an external device via any suitable protocol including, but not limited to, Ethernet, Universal Serial Bus (USB), or FireWire (IEEE 1394) communications protocols. The interface unit 60 may also include a display 67, a driver module 66 for light emitting diodes (LEDs) and corresponding LEDs, or a combination thereof to provide a visual indication of the coordinates and insertion depth 92 of a needle via the needle insertion location system 30. It is further contemplated that the interface unit 60 may include various configurations of some or all of the above-described elements without deviating from the scope of the invention. For example, the interface unit 60 may include one of the wireless module 63 or the port interface 64 and may similarly include one of the display 67 or the LED driver 66.

The grid plate 32 is configured to be removably inserted into an opening proximate to the anatomical region to be imaged. According to the embodiment illustrated in FIG. 2, the grid plate 32 may be inserted into an opening 26 in a compression plate 24 or another portion of the support structure 10. In this embodiment, the interface unit 60 may be integrally formed with the compression plate 24 or with the other portion of the support structure 10. According to another embodiment of the invention, the interface unit 60 may be integrally formed with the grid plate 32 and the entire needle insertion location system 30 is insertable into the opening 26 in the compression plate 24 or the other portion of the support structure 10. An outer frame 31 is configured to enclose, for example, the interface unit 60 and include the grid indication unit 70. The outer periphery of the outer frame 31 is configured to slidably engage the opening 26 in the compression plate, and an opening 33 in the outer frame 31 is configured to receive the grid plate 32. According to yet another embodiment of the invention, the grid plate 32 may be integrally formed with the needle insertion location system 30.

The needle insertion location system 30 further includes a grid indication unit 70 which provides a visual indication of the opening 40 in which the grid block 50 is to be inserted and of the aperture 52 within the grid block 50 in which the needle 56 is to be inserted. Referring to FIG. 4, one embodiment of the grid indication unit 70 includes an alpha-numeric display 80 configured to identify the row 25 and column 29 within the array 42 of openings 40 in the grid plate 32 in which the grid block 50 is to be inserted. The display 80 may be of any suitable type including, but not limited to, a liquid-crystal display (LCD), an LED display, or an organic light-emitting diode (OLED) display. Each row 25 includes a row indicia 23 which may be a letter, number, symbol, or combination thereof. Each column 29 includes a column indicia 27 which may be a letter, number, symbol, or combination thereof. The alpha-numeric display 80 is configured to display the row indicia 23 and the column indicia 27. A portion of the display 80 may also be configured to display an array of circles, or other shapes, corresponding to the apertures 52 in the grid block 50. Optionally, the grid indication unit 70 may include multiple light sources 82, such as LEDs, arranged in a configuration corresponding to the apertures 52 in the grid block 50.

Figure 5:
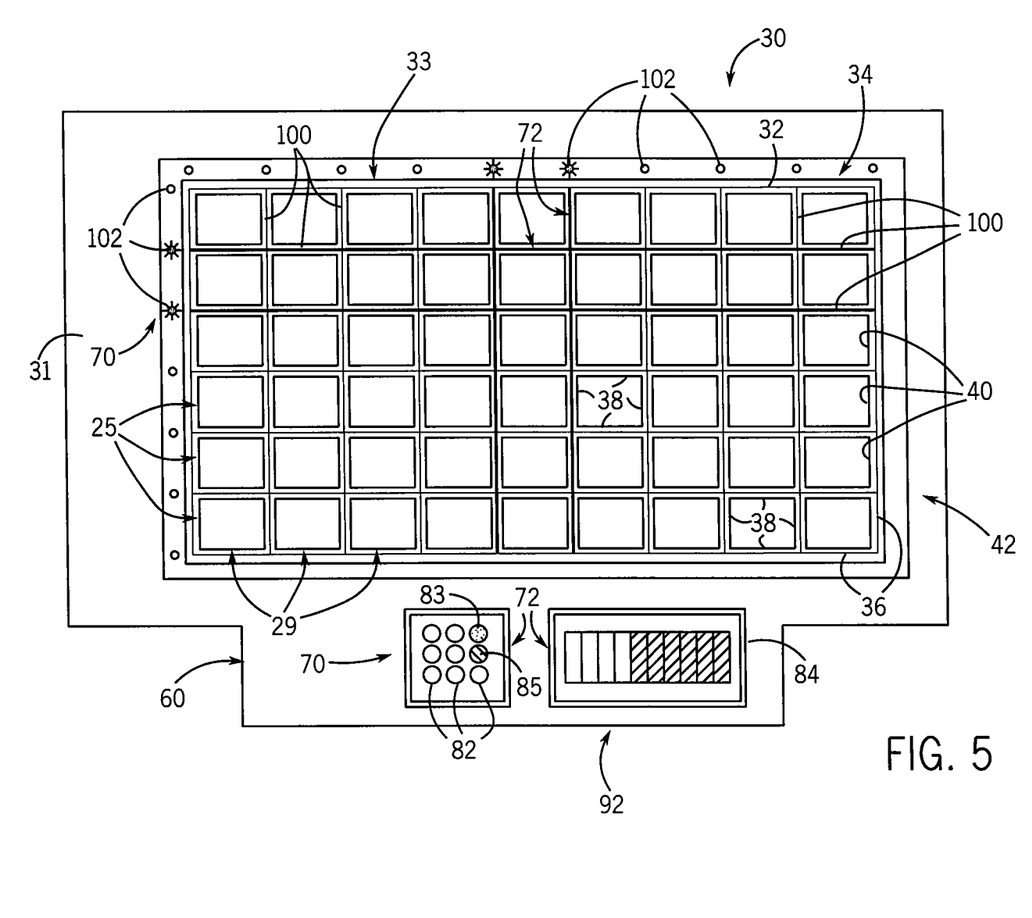
FIG. 5 is a front elevation view of a needle insertion system according to another embodiment of the invention.
Figure 6:
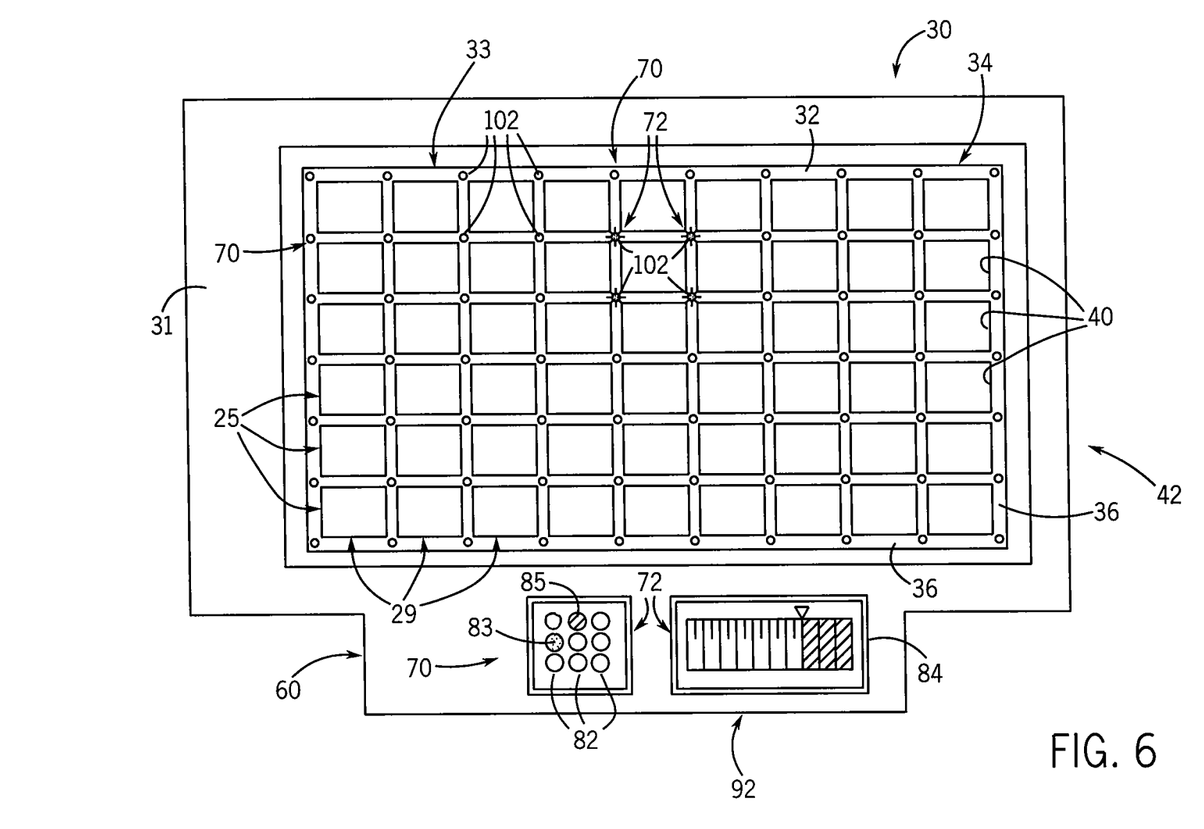
FIG. 6 is a front elevation view of a needle insertion system according to another embodiment of the invention.

Referring next to FIG. 5, another embodiment of the grid indication unit 70 includes light guides 100 mounted to or integrally formed along each of the grid walls 38. A light source 102, such as an LED, mounted at the end of each light guide 100 emits light into and along the light guide 100. The light sources 102 and light guides 100 cooperate to identify the row 25 and column 29 within the array 42 of openings 40 in the grid plate 32 in which the grid block 50 is to be inserted. Referring next to FIG. 6, another embodiment of the grid indication unit 70 includes multiple light sources 102, such as LEDs, configured to identify the row 25 and column 29 within the array 42 of openings 40 in the grid plate 32 in which the grid block 50 is to be inserted. Each light source 102 is mounted at an intersection between grid walls 38.

The grid indication unit 70 further includes a display 84 corresponding to an insertion depth 92 of the needle 56. As illustrated in FIG. 4, the display 84 may be alpha-numeric and indicate the insertion depth 92 in millimeters. Optionally, any other unit corresponding to a depth indicator on the needle 56 may be displayed. As illustrated in FIGS. 5 and 6, the display 84 may be a bar graph or other metric that represent corresponding gradations 59 on the needle 56. A portion of the display 84 may be lit or an arrow may be provided to indicate the depth along the displayed metric at which the needle is to be inserted. According to yet another embodiment of the invention, the display 84 may be configurable and display different metrics according to the type of needle 56 used for the procedure.

Figure 7:
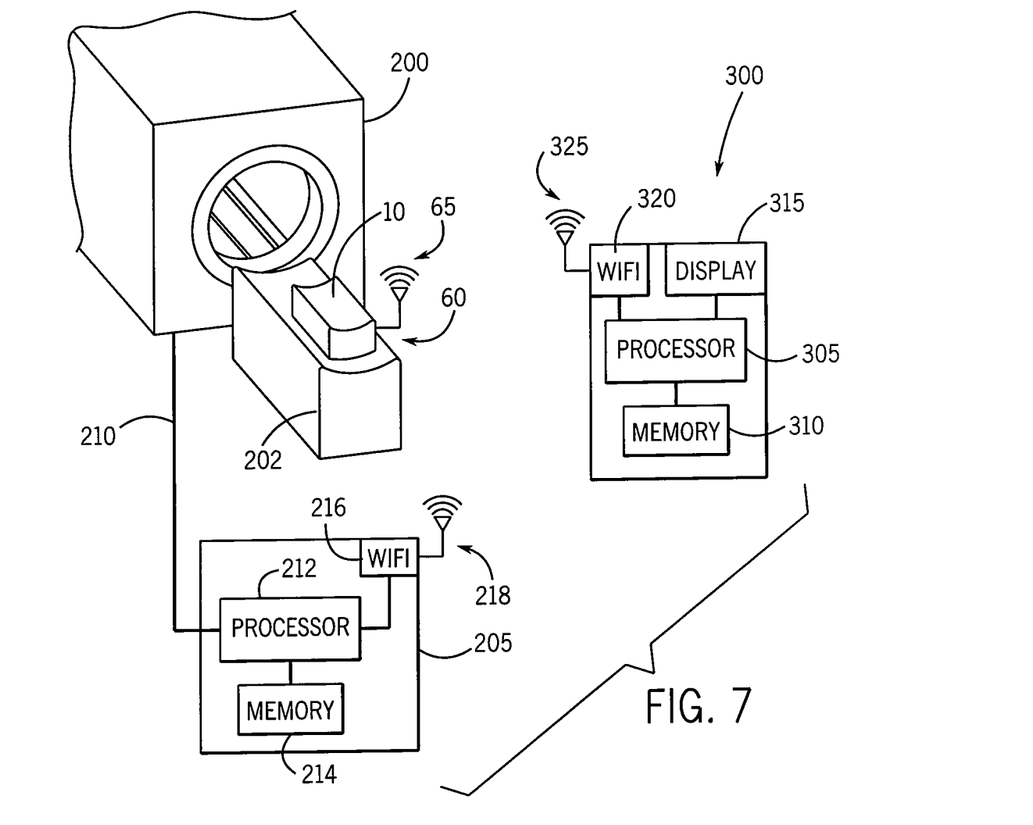
FIG. 7 is a block diagram representation of an exemplary MRI scanner incorporating a needle insertion system according to one embodiment of the invention.

Referring next to FIG. 7, an exemplary environment incorporating one embodiment of the invention is illustrated in block diagram form. An MRI scanner 200 is in communication with a control unit 205 via a communication cable 210. The communication cable 210 may include electrical or fiber-optic conductors, shielded to prevent interference between the cable 210 and the MRI scanner 200. The control unit 205 may be a computer having a processor 212 executing one or more programs stored in memory 214. The control unit 205 controls the MRI scanner 200 to obtain MRI images of an anatomical region. The control unit 205 may also provide a user interface to permit an MRI technician to place a marker on the MRI images. The marker identifies a target area within the imaged anatomical region on which the procedure is to be performed. Optionally, the MRI image may be transmitted to a remote device and the remote device may provide a user interface to permit the MRI technician to place the marker on the MRI images. The control unit 205 further includes a wireless module 216 configured to transmit and/or receive data using a Wi-Fi technology established, for example, by the IEEE 802.11 family of standards. Optionally, the wireless module 216 may be configured to transmit and/or receive data using any other suitable protocol established, for example, by the Bluetooth® standard. The wireless module 216 transmits and/or receives communications via at least one antenna 218 connected to and typically integrated with the wireless communication module 216. Optionally, the antenna 218 may be a separate device either internal to or external from the control unit 205.

According to the illustrated embodiment, a remote device 300 is in communication with both the control unit 205 and the interface unit 60. The interface unit 60 is located in the support structure 10, which is, in turn, positioned on a table 202 for use with the MRI scanner 200. The remote device 300 is a portable processing device such as a tablet computer, a notebook computer, or a laptop computer. The remote device 300 includes a processor 305 executing one or more programs stored in memory 310. The remote device 300 receives an MRI image and a marker from the control unit 205. The remote device 300 executes one or more programs to determine needle insertion information 72 as a function of the MRI image, marker, and grid plate 32 to be used and transmits the needle insertion information 72 to the interface unit 60. The remote device 300 further includes a wireless module 320 configured to transmit and/or receive data using a Wi-Fi technology established, for example, by the IEEE 802.11 family of standards. Optionally, the wireless module 320 may be configured to transmit and/or receive data using any other suitable protocol established, for example, by the Bluetooth® standard. The wireless module 320 transmits and/or receives communications via at least one antenna 325 connected to and typically integrated with the wireless communication module 320. Optionally, the antenna 325 may be a separate device either internal to or external from the remote device 300. The remote device 300 may further include a display 315 and include one or more programs configured to display, for example, the MRI image and marker and/or the needle insertion information 72 to an operator. Further, the display 315 may be a touch-screen or still other user interfaces may be provided to receive input from or provide output to an operator. According to another embodiment of the invention, one or more programs may be included on the control unit 205 to perform the functions of the remote device 300 and to communicate directly with the interface unit 60.

In operation, the needle insertion location identification system 30 is configured to automatically determine insertion information from an MRI image and corresponding marker. The MRI image corresponds to an anatomical region being imaged by the MRI scanner 200. A data file containing the MRI image is transmitted to the remote device 300 for processing. The data file containing the MRI image may include other data, such as the layer, or depth, of the image from within the anatomical region as well as the location of a marker placed by an MRI technician, identifying a target area at which a procedure, such as a biopsy, is to be performed. Optionally, separate files may include MRI image information and the corresponding data.

The remote device 300 executes a program on the remote processor 305 to process the MRI image and associated data to determine needle insertion information 72. The MRI image was obtained by one or more antennas and/or antenna arrays located near the anatomical region being imaged. According to one embodiment of the invention, the antennas and/or antenna arrays are located within the compression plates 22, 24 and/or the stationary plate 20, and the grid plate 32 is positioned in a known relationship to the antennas and/or antenna arrays. The relationship between the antennas and/or antenna arrays and the grid plate 32 is stored in the memory 310 of the remote device 300. Optionally, a database may be stored in the memory 310 identifying multiple antenna configurations and multiple needle insertion location system 30 configurations. The remote device 300 may include a setup screen and user interface to receive configuration information from an operator. The configuration information may include, but is not limited to, the antenna configurations, the type of needle 56 to be used, and the needle insertion location system 30 configuration.

The remote processor 305 executes a program utilizing, for example, the boundaries of the image to determine a relationship of the anatomical region being imaged to the selected antennas and/or antenna arrays. The program executing on the remote processor 305 retrieves the marker information to identify the target area in the anatomical region. The remote processor 305 further utilizes the system configuration and the relationship between the grid plate 32 and the antennas and/or antenna arrays to subsequently relate the target area of the anatomical region to a specific insertion location, defining an opening 40 in the grid plate 32 and an aperture 52 in the grid block 50. The remote processor similarly identifies the insertion depth 92 as a function of the MRI image and system configuration. Thus, the needle insertion information 72 includes an opening 40 in the grid plate 32, an aperture 52 of the grid block 50, and the insertion depth 92.

The remote processor 305 may further be configured to determine a desired needle orientation during the procedure. Referring again to FIG. 3, the opening 57 in the needle faces radially outward along a portion of the needle 56. As illustrated, the opening 57 faces upward; however, it may be desirable to rotate the needle about its central axis such that the opening 57 faces toward one side or the other, downward, or at any orientation therebetween. Although one of the apertures 52 within the grid block 50 is selected as a desired insertion point, the grid block 50 provides a finite resolution. The location of the lesion may be, for example, evenly spaced between two adjacent apertures 52 or behind one of the grid walls 38 of the grid plate. The remote processor 305 selects the opening 40 within the grid plate for insertion of the grid block 50 and the aperture 52 within the grid block that most closely corresponds to the target region. In the instance, for example, when a target region is evenly spaced between adjacent apertures 52, either of the two apertures 52 may be selected for insertion of the needle 56. It would then be desirable to orient the needle 56 such that the opening 57 faces the other of the two apertures 52. The needle orientation information may also be included in the needle insertion information.

The remote device 300 transmits the needle insertion information 72 to the interface unit 60 to provide a visual indication of the insertion location and depth to the MRI technician or other medical personnel. The remote device 300 establishes wireless communications with the interface unit 60 between respective wireless modules 320 and 63. The needle insertion information 72 is then wirelessly transmitted from the remote device 300 to the interface unit 60. The grid indication unit 70 then provides a visual indication of the insertion location and insertion depth to the MRI technician or other medical personnel. Thus, the needle insertion location identification system 30 determines the insertion location and depth from an MRI image and automatically provides a visual indication of the insertion location and depth to the MRI technician or other medical personnel.

Referring again to FIG. 4, a first embodiment of the interface unit 60 includes an alpha-numeric display 80 of the opening 40 for the insertion location. Each row indicia 23 is a letter and each column indicia 27 is a number. The letter and number of the opening 40 corresponding to the insertion location is provided on the display 80. According to one embodiment of the invention, the alpha-numeric display 80 also includes a graphical representation of the array of apertures 52 on the grid block. Each aperture is identified by a circle on the display. A first visual indicator 83 is placed on one of the apertures 52 indicating which of the apertures 52 is to receive the needle 56. A second visual indicator 85 is placed on another of the apertures 52 indicating the orientation of the needle 56. If the display 80 is a color display, the visual indicators 83, 85 may be different colors. If the display 80 is black and white, or gray-scale, each visual indicator 83, 85 may be, for example, a different pattern or different shade. According to another embodiment of the invention, the interface unit 60 may include an array of LEDs 82 arranged according to the configuration of apertures 52 in the grid block. The LEDs 82 may be multi-color LEDs such that the one of the LEDs 82 may be energized in a first color to provide the first visual indicator 83 and another of the LEDs 82 may be energized in a second color to provide the second visual indicator 85. Optionally, if single color LEDs are utilized, one LED 82 may be continuously energized and the other pulsed to provide the first and second visual indicator 83, 85. It is contemplated that various other first and second visual indicators 83, 85 may utilized without deviating from the scope of the invention. The interface unit 60 also provides a display unit 84 giving a visual indication of the insertion depth 92.

Referring next to FIG. 5, another embodiment of the interface unit 60 includes multiple LEDs 102 positioned around a perimeter of the grid plate 32 with each LED 102 aligned with one of the grid walls 38 and with each of the outer walls 36. A light guide 100 is mounted along each of the grid walls 38 and each of the outer walls 36. Each LED 102 on opposite sides of the row 25 and on opposite sides of the column 29 of the opening 40 corresponding to the insertion location are energized. The light emitted from the LEDs 102 is conducted along the corresponding light guide 100 such that each edge of the opening 40 corresponding to the insertion location is surrounded by an energized light guide. Optionally, a single LED 102 along each row 25 and column 29 may be energized such the intersection of the illuminated light guides 100 indicate, for example, the top, left corner of the opening 40 corresponding to the insertion location. According to one embodiment of the invention, a display unit may provide a graphical representation of the array of apertures 52 on the grid block as discussed above with respect to FIG. 4. Optionally, the interface unit 60 may include an array of LEDs 82 arranged according to the configuration of apertures 52 in the grid block. The interface unit 60 provides the first and second visual indicators 83, 85 as discussed above with respect to FIG. 4. The display unit 84 for the insertion depth 92 is configured as a bar-graph with the insertion depth corresponding to the illuminated bars on the graph.

Referring next to FIG. 6, yet another embodiment of the interface unit 60 includes multiple LEDs 102, each LED being positioned at an intersection of the grid walls 38. At least one LED 102 proximate to the opening 40 corresponding to the insertion location is energized. As illustrated, each of the LEDs 102 at an intersection of grid walls 38 proximate to the opening 40 is illuminated. The interface unit 60 may include either a display or an array of LEDs 82 corresponding to the configuration of apertures 52 in the grid block. The interface unit 60 provides the first and second visual indicators 83, 85 as discussed above with respect to FIG. 4. The display unit 84 for the insertion depth 92 is configured as a ruled display, corresponding, for example to a scale printed on a needle with the portion of the needle to be inserted being illuminated.

The above-described needle insertion location system 30 provides an automated method of identifying the desired insertion point and insertion depth for performing a medical procedure guided by diagnostic imaging. Although the invention is discussed herein with respect to an MRI guided medical procedure, such as a biopsy, it is contemplated that the needle insertion system 30 may be utilized with other medical diagnostic imaging technology including, but not limited to ultrasound or Positron Emission Tomography (PET)/MRI imaging. The physical apparatus is first arranged to receive a patient. For example, the grid plate 32 or needle insertion system 30 is inserted into the opening 26 in a compression plate 24 according to a desired configuration and application requirement, and the physical configuration is entered into the remote device 300. A patient is positioned on the support structure and the anatomical region on which the biopsy is to be performed is immobilized. An MRI image of the anatomical region is obtained and displayed on the MM control unit 205. The MRI technician places a marker on the MM image identifying the target area on which the biopsy is to be performed. The MRI image and marker information is transmitted to the remote device 300. The remote device 300 processes the MRI image, marker information, and system configuration to determine the needle insertion information 72. The remote device 300 transmits the needle insertion information 72 to the configuration unit 60. The configuration unit 60 then provides a visual indication on the grid indication unit 70 of the opening 40 in the grid plate 32 and the aperture 52 in the grid block 50 in which the needle is to be inserted, and the needle insertion depth 92 is displayed is display unit 84. The MRI technician inserts the grid block 50 in the identified opening 40 and inserts the needle 56 in the identified aperture 52 of the grid block 50 to the depth shown on the display unit 84. The biopsy is performed and the needle removed. Thus, the needle insertion location system 30 provides an automated indication of the needle insertion location and depth to the MRI technician as a function of an MRI image and target area identified on the MRI image.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A needle insertion location identification system for use with a support structure, wherein the support structure is configured to be positioned on an imaging table and to position a patient during a medical procedure guided by diagnostic imaging, the needle insertion location identification system comprising:
 a frame removably mounted to the support structure;
 a grid plate including a plurality of openings arranged in an array, the grid plate located in the frame;
 a grid block configured to be inserted into one of the openings in the grid plate, the grid block including a plurality of apertures, each aperture configured to receive a needle; and
 an interface unit enclosed within one of the frame and the support structure, wherein the interface unit includes:
  a wireless module;
  a memory device storing a plurality of instructions;
  a local processor in communication with the wireless module and the memory device, the local processor operative to execute the plurality of instructions to:
   establish a wireless communication connection between the wireless module remote processor, and
   receive needle insertion information from the remote processor via the wireless communication connection, wherein the needle insertion information includes a first identifier corresponding to one of the openings and a second identifier corresponding to one of the apertures in which the needle is to be inserted; and
  a grid indication unit in communication with the local processor, wherein:
   the grid indication unit is adjacent to the grid plate,
   the grid indication unit receives the first identifier and the second identifier from the local processor, and
   the grid indication unit has a display on which the first identifier and the second identifier are displayed adjacent to the grid plate while performing the medical procedure.

2. The needle insertion location identification system of claim 1, wherein the needle insertion information further includes a third identifier corresponding to an insertion depth and the grid indication unit is further configured to display the third identifier adjacent to the grid plate while performing the medical procedure.

3. The needle insertion location identification system of claim 1 wherein the needle insertion information further includes a third identifier corresponding to a needle orientation and the grid indication unit is further configured to display the third identifier adjacent to the grid plate while performing the medical procedure.

4. The needle insertion location identification system of claim 1 wherein the grid indication unit includes:
 a plurality of row indicia,
 a plurality of column indicia,
 each of the row indicia corresponds to a row in the array and is located adjacent to its corresponding row,
 each of the column indicia corresponds to a column in the array and is located adjacent to its corresponding column,
 the first identifier of the needle insertion information includes one of the row indicia and one of the column indicia.

5. The needle insertion location identification system of claim 1 wherein the array of openings on the grid plate includes a plurality of rows and a plurality of columns, the needle insertion location identification system further comprising:
 a plurality of light guides wherein at least one light guide extends along each row of the array and at least one light guide extends along each column of the array; and
 a plurality of light sources, wherein each light source corresponds to one of the light guides and is configured to emit light along the light guide, wherein the grid indication unit is configured to control each of the light sources to emit light along the light guide extending along the row and the light guide extending along the column of the opening identified in the needle insertion information.

6. The needle insertion location identification system of claim 1 further comprising a plurality of light sources wherein at least one of the light sources corresponds to each of the openings in the grid plate.

7. The needle insertion location identification system of claim 6 wherein:
   each of the light sources is a light emitting diode (LED), one of the LEDs is placed at each intersection between a row and a column in the array of openings, and
   the visual indication of the opening is provided by energizing each of the LEDs placed at the intersections around the opening.

8. The needle insertion location identification system of claim 1 wherein the grid indication unit includes a plurality of LEDs arranged to correspond to an arrangement of the apertures in the grid block and wherein one of the LEDs is energized to provide the visual indication of the aperture identified by the needle insertion information.

9. The needle insertion location identification system of claim 1 further comprising:
   at least one diagnostic antenna mounted in the support structure and operable to transmit signals during diagnostic imaging to a control unit for a magnetic resonance imaging (MRI) scanner operable to perform the diagnostic imaging, wherein the signals transmitted from the diagnostic antenna are used to generate at least one MRI image;
   a remote device in communication with the control unit and the interface unit, wherein the remote device includes:
      a wireless module operable to wirelessly receive a data file from the control unit, wherein the data file includes the at least one MRI image and wherein the MRI image includes coordinate data with respect to the MRI scanner;
      a memory operable to store a relationship between the grid plate and a target area in the MRI image; and
      a processor operable to determine the needle insertion information as a function of the at least one MRI image and the relationship between the grid plate and the target area in the MRI image, wherein the processor of the remote device is the remote processor of claim 1 and wherein the wireless module is further operable to transmit the needle insertion information to the interface unit.

10. The needle insertion location identification system of claim 1 wherein the medical procedure is performed in a magnetic resonance imaging environment.

11. A block identification system for use with a support structure configured to be positioned on an imaging table and to position a patient during a medical procedure guided by diagnostic imaging, the block identification system comprising:
   a frame removably mounted to the support structure;
   a grid plate including an outer periphery defined by a plurality of outer walls and a plurality of intersecting grid walls, each grid wall extending between a first outer wall and a second outer wall, wherein the plurality of intersecting grid walls define a plurality of openings therebetween and wherein the grid plate is located in the frame;
   at least one grid block configured to be inserted into one of the openings in the grid plate, the grid block including a plurality of apertures;
   a grid indication unit adjacent to the grid plate;
   a memory device enclosed within one of the frame and the support structure, the memory device storing a plurality of instructions; and
   a local processor enclosed within one of the frame and the support structure, the local processor in communication with the memory device and operative to execute the plurality of instructions to:
      establish a communication connection with a remote processor,
      receive insertion information from the remote processor via the communication connection, wherein the insertion information identifies one of the openings on the grid plate and one of the apertures on the grid block, and
      display the insertion information on the grid indication unit adjacent to the grid plate to provide a visual indication of one of the openings and one of the apertures in which a needle is to be inserted.

12. The block identification system of claim 11 wherein each of the openings includes a grid block.

13. The block identification system of claim 11 wherein the plurality of openings defines a two-dimensional array and wherein the block identification system further comprises:
   a first set of indicia identifying openings along a first dimension of the array; and
   a second set of indicia identifying openings along a second dimension of the array.

14. The block identification system of claim 13 wherein the grid indication unit displays one of the first set of indicia and one of the second set of indicia corresponding to the opening identified by the insertion information.

15. The block identification system of claim 11, wherein the insertion information further includes an insertion depth and the grid indication unit is further configured to provide a visual indication of the insertion depth.

16. The block identification system of claim 11, wherein the insertion information further includes a needle orientation and the grid indication unit is further configured to provide a visual indication of the needle orientation.

17. The block identification system of claim 11 further comprising:
   at least one diagnostic antenna mounted in the support structure and operable to transmit signals during diagnostic imaging to a control unit for a magnetic resonance imaging (MRI) scanner operable to perform the diagnostic imaging, wherein the signals transmitted from the diagnostic antenna are used to generate at least one MRI image;
   a remote device in communication with the control unit and the grid indication unit, wherein the remote device includes:
      a wireless module operable to wirelessly receive a data file from the control unit, wherein the data file includes at least one MRI image, wherein the MM image includes coordinate data with respect to the MRI scanner;
      a memory operable to store a relationship between the grid plate and a target area in the MRI image; and
      a processor operable to determine the insertion information as a function of the at least one MRI image and the relationship between the grid plate and the target area in the MRI image, wherein the processor of the remote device is the remote processor of claim 11 and wherein the wireless module is further operable to transmit the insertion information to the grid indication unit.

18. The block identification system of claim 17 wherein the remote device is a tablet computer.

19. The block identification system of claim 11 further comprising a plurality of light sources, wherein each light source corresponds to at least one of the openings in the grid plate and wherein the grid indication unit is configured to selectively energize each of the light sources to provide the visual indication of the opening identified in the insertion information.

20. The block identification system of claim 19 wherein:
each of the plurality of light sources is a light emitting diode (LED),
one of the LEDs is placed at each intersection between the grid walls, and
the visual indication of the opening is provided by energizing at least one of the LEDs proximate to the identified opening.

21. The block identification system of claim 19 further comprising a plurality of light guides wherein:
each light guide is mounted along one of the grid walls,
each light source corresponds to one of the light guides and is configured to emit light along the light guide, and
the grid indication unit is configured to control each of the light sources to emit light along at least one of the light guides proximate to the identified opening.

* * * * *